United States Patent [19]

Morita et al.

[11] Patent Number: 4,908,115
[45] Date of Patent: Mar. 13, 1990

[54] MINUTE ELECTRODE FOR ELECTROCHEMICAL ANALYSIS

[75] Inventors: Kenichi Morita; Yoshihiro Shimizu, both of Kanagawa, Japan

[73] Assignee: Toray Industries, Inc., Japan

[21] Appl. No.: 143,154

[22] PCT Filed: Apr. 21, 1987

[86] PCT No.: PCT/JP87/00252

§ 371 Date: Feb. 22, 1988

§ 102(e) Date: Feb. 22, 1988

[87] PCT Pub. No.: WO87/06701

PCT Pub. Date: Nov. 5, 1987

[30] Foreign Application Priority Data

Apr. 22, 1986 [JP] Japan .................................. 61-92676

[51] Int. Cl.[4] ........................ G01N 27/46; C25B 11/12
[52] U.S. Cl. .................................... 204/294; 204/400; 204/403; 204/415; 204/435
[58] Field of Search ............... 204/400, 403, 415, 435, 204/294

[56] References Cited

U.S. PATENT DOCUMENTS

| | | | |
|---|---|---|---|
| 3,129,161 | 4/1964 | Anderson et al. | 204/435 |
| 3,838,033 | 9/1974 | Mindt et al. | 204/403 |
| 4,016,063 | 4/1977 | Radnoti | 204/428 |
| 4,108,757 | 8/1978 | Fleet et al. | 204/294 |
| 4,121,989 | 10/1978 | Shum et al. | 204/428 |
| 4,369,104 | 1/1983 | Beckley | 204/294 |
| 4,431,508 | 2/1984 | Brown, Jr. et al. | . |
| 4,439,303 | 3/1984 | Cocchi | 204/294 |
| 4,473,450 | 9/1984 | Nayak et al. | 204/294 |
| 4,505,784 | 3/1985 | Mund et al. | 204/415 |
| 4,561,963 | 12/1985 | Owen et al. | . |
| 4,680,100 | 7/1987 | Morin | 204/294 |

FOREIGN PATENT DOCUMENTS 0197747 10/1986 European Pat. Off. .

Primary Examiner—T. Tung
Attorney, Agent, or Firm—Austin R. Miller

[57] ABSTRACT

A minute electrode comprised of a bundle of carbon fibers covered with a nonconducting resin, and the ends of the carbon fibers recesses at one end of the resin, and has the micro-holes released to the outside.

This electrode has small flow sensitivity and is not subject to be contaminated by interference substances.

The minute electrode of this invention is useful for various electrodes for the electrochemical analysis.

12 Claims, 2 Drawing Sheets

MINUTE ELECTRODE FOR ELECTROCHEMICAL ANALYSIS

TECHNICAL FIELD

This invention relates to an improved minute electrode such as a dissolved oxygen measuring electrode, or an ion concentration measuring electrode, for biosensors and as a reference electrode which has low flow sensitivity and also protection from contamination.

BACKGROUND ART

The analysis of oxygen, saccharide, amino acid, pH etc. has hitherto been done by an electrochemical method, using several kinds of electrodes. Following is the explanation of prior techniques for various kinds of electrodes and sensors.

(1) Sensor for measuring the concentration of dissolved oxygen

It is important to measure the concentration of dissolved oxygen in a body fluid such as blood, or that of a culture fluid in a fermenter jar. Clark type oxygen sensor has been used widely. The composition of this sensor is as follows.

The container of the sensor is filled with an electrolyte such as a caustic alkaline solution etc., and the cathode (for example made of platinum) and the anode (for example made of lead etc.) are set therein, and separated from outside (the solution which should be measured) by a gas permeable membrane made of polytetrafluoroethylene etc.. The concentration of oxygen can be determined by measuring the electric current between the two electrodes, whereas oxygen molecules pass from the test solution to the inside of the sensor container through a selective permeable membrane, and is reduced electrochemically on the platinum electrode surface. By the appearance of this method, the amount of oxygen can be determined easily, but there are still the following problems such as, instability of pressure at sterilization, difficulty of maintenance, limitation for miniaturization, inability to determine the real dissolved oxygen concentration, except for partial oxygen pressure, inability to determine the dissolved oxygen concentration in fermentation under pressure or on the bottom of the sea and difficulty because the lakes, and the variation of the electric current is rather large in relation to temperature change.

Several methods are proposed for other oxygen concentration measuring electrodes, especially for body fluids. One is a method to make the condition of stable contact by means of covering the fine metal wire electrode surface with porous materials consisting of many layers (see Japanese Unexamined Patent Publication No. 57-117838). Another is a method to insert the fine metal wire electrode into the opened tube in the recessed position from the tip of the said electrode (see Japanese Unexamined Patent Publication No. 57-195436).

However, these methods have still several problems such as contamination of the electrode and the possibility of suffering from iatrogenic disease by peeling off the porous membrane.

(2) The sensor for measuring the concentration of ions A glass electrode has been widely used for measuring the concentration of hydrogen ions. However, this has the following several problems. That is, it is easy to break, also it is easy to contaminate, and it has limitations when used in alkali aqueous solution. Moreover, it is very difficult to miniaturize, because the glass electrode needs an inside standard solution compartment. And there is a possibility that the inside standard solution may flow out.

Recently, the following phenomena has been discovered: A membrane, which is deposited by means of electrochemical polymerization on the surface of the electrode, causes a change in potential in accordance with bonding or removing the hydrogen ion. [William R. Heineman, Anal. Chem. 52, 345 (1980)] The following pH sensor was also proposed. The method has applied the following phenomena wherein the membrane, which is formed on the surface of an electrode, causes a reversible oxidation/reduction reaction with bonding or removing of hydrogen ion (see Japanese Unexamined Patent Publication No. 61-19434). However, when these pH sensors are used continuously in body fluids or fermentative solution, a potential drift occurs in accordance with contamination.

(3) Bio-sensor

There are two types of bio-sensors. That is, the first one is used to determine the concentration of materials related to a biochemical reaction, by measuring the current caused in an electrochemical reaction of said materials.

The other one is to analyze the electroactive materials (related to biochemical reaction), by measuring the potential of the membrane which selectively responds to said materials. The former one is called an "Amperometry method" and in this case, an oxygen sensor and a hydrogen peroxide electrode are applied. On the other hand, the latter one is called a "Potentiometry type" and an ion selective electrode and an ammonia or carbon dioxide gas electrode (which consists of some kind of gas permeable membrane and pH electrode) are applied.

Enzyme, microorganism, and antigenantibody reaction are one of the biochemical reactions. The bio-sensor has problems as said hereinbefore, whereas a fundamental composition of a bio-sensor is an oxygen sensor or a pH electrode.

(4) The reference electrode

Conventional reference electrodes have the following problems; 1) they are easy to break, 2) they are hard to ensure for the pressure of sterilization, whereas the saturated calomel electrode and silver/silver chloride electrode etc. includes an inside-solution.

Therefore, an object of the present invention is to provide various types of electrodes and also sensors which can determine for example, the dissolved oxygen, saccharide, amino acid, pH etc. stably and accurately without disadvantages of prior techniques.

DISCLOSURE OF THE INVENTION

The present invention relates to a minute electrode for electrochemical analysis comprised of a carbon fiber bundle covered with a nonconducting resin, and the ends of carbon fibers are recessed from one end of said bundle, and microholes released to the outside are made on the carbon fibers. The minute electrode which has low flow sensitivity and protects from electrode contamination by interference substances can be obtained in accordance with this composition.

BEST MODE FOR CARRYING OUT THE INVENTION

Figure 1:
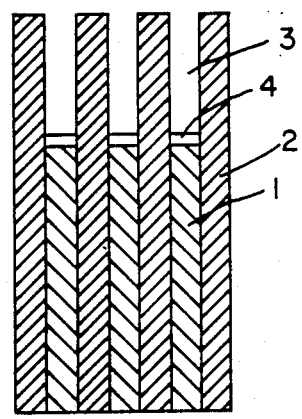
FIG. 1 shows a conceptual illustration of a minute electrode of the present invention.

Conceptually, a minute electrode of this invention is shown in FIG. 1. The bundle of carbon fibers consists of plural carbon fibers 1 and nonconducting resin 2. In the same FIG. 1, the top of carbon fiber 1 is recessed from the top of nonconducting resin 2 and forms the microhole 3 which is released to the outside. And the bottom of this micro-hole which is the top part of the carbon fiber becomes the electrode surface. If desired, the surface of the electrode may be modified by an electrocatalyst 4 for electrochemical reactions. This electrode is hereinafter referred to as "basic electrode".

Though there is no limitation upon the carbon fibers which form the basic electrode, the following carbon fibers such as polyacrylonitrile based, pitch based, rayon based, phenol resin based etc. and also fibers produced by the vapour deposition method, are used preferably.

The nonconducting material is preferably selected from fluorinated resin, polyester resin, epoxy resin, polyphenyleneoxide resin, polyphenylenesulfide resin, urethan resin, silicon resin, vinylchloride resin, phenol resin etc.. When the minute electrode is used in the living body, a high quality anti-thrombogenesity resin is most preferable.

The plural carbon fibers are covered with a nonconducting resin, and it is subjected to a heat-set process in order to form one body. The cross-section of that (body) is like islands (each carbon fiber) in a sea (the nonconducting resin). Namely, carbon fibers do not contact each other. The number of carbon fibers is usually in the range of from 50 to 50,000, and is selected on purpose of use. And when this electrode is used as a reference electrode, sometimes more than 50,000 carbon fibers may be used.

Generally, the ratio of the carbon fiber's area in the cross-section of this electrode is in the range of from 3 to 60%. The diameter of the carbon fiber is less than 20 $\mu$m, and more preferably it is less than 10 $\mu$m.

The diameter of carbon fiber is that of micro-hole and in case of less than 20 $\mu$m, it causes so called "filter effect".

Generally, the depth of the micro-hole is in the range of from 0.5 to 500 $\mu$m, and more preferably it is in the range of from 20 to 400 $\mu$m. It is no problem, for example, if it is sharp like a pencil or in opposition it is hollowed. But in this case, the depth of the microhole is defined by its deepest part.

If desired, the surface of the electrode is coated with an electrocatalyst. And that material may be selected from platinum, silver, gold, iridium, phthalocyanine and its derivatives etc.. The ability of oxygen reduction catalysis becomes higher in accordance with making this layer.

The basic electrode in this invention is kept more resistant to contamination by means of covering electrode surface with selective permeable membrane. It is desirable that this membrane is a polymer made by electrochemical polymerization.

For example, the basic electrode in this invention can be obtained by the following procedure.

At first, the bundle of the carbon fiber is impregnated with a nonconducting resin which includes a hardening agent, then the bundle is subjected to heat treatment in order to harden the resin. In this way, a wire like carbon fiber bundle which is covered with nonconducting resin is obtained. Then the carbon fiber bundle is cut to a desired length, then one end of this bundle is burnished, and the lead wire is bonded by using silver paste to the other end. On the burnished side of the bundle, the micro-holes are formed by etching the carbon fibers by means of electrochemical oxidation which is illustrated hereinafter.

Electrolytic solutions may be selected from acid or alkaline solutions, and alcohols such as methanol which includes a supporting electrolyte. Then the anodic oxidation is done. In this process, the carbon fiber is connected to the anode, and the metal electrode is used as a counter electrode. The oxidation voltage is preferably in the range of from 1 to 100 volts. Also it is preferable that the oxidation and reduction are repeated in turns.

When the surface of the electrode is coated with the electrocatalyst, the following method such as plating, vacuum evaporation, sputtering etc. is applicable.

Including the basic electrode and also other electrodes, the micro-hole may be filled up with gelatinoid material. Gelatinoid materials may be selected from agar, gelatin, polyacrylamide gel etc..

Various electrodes of the present invention are illustrated below more concretely.

(1) An electrode for measuring the concentration of dissolved oxygen

The basic electrode itself may be applied as the electrode for measuring the concentration of dissolved oxygen. But more preferably, the surface of the basic electrode is coated with a selective permeable membrane by an electrochemical polymerization process. The best method of electrochemical polymerization is as follows. The supporting electrolyte such as sodium perchlorate or sodium sulfate is dissolved in an organic solvent such as acetonitrile etc. or water, and the monomer compound which should be electrochemically polymerized is added and this mixed material is electrochemically polymerized at a constant potential of 1 to 1.5 volt. There is no limitation, if the polymer doesn't have electroactivity and also it is a selective permeable membrane which protects the electrode surface from contamination. Monomer compound usable for present invention is selected from amino-containing aromatic compounds or hydroxy aromatic compound for example, 4,4'-diaminodiphenylether, 4,4'-diaminodiphenylsulfide, phenol, aniline, or phenol derivatives, aniline derivatives. In accordance with polymerization conditions, the electroactive membrane will be formed. For example, when aniline is used as the monomer, an alkaline or neutral condition should be adopted, otherwise the membrane has electroactivity.

Repeating the polymerization is preferable, whereas it makes the membrane coating complete and also makes the selective permeability higher.

When an oxygen sensor is made by using said electrode, silver/silver chloride is combined as a counter electrode. This electrode may be applicable not only for measuring the dissolved oxygen but also other electrochemical reactant materials, by means of changing the selective permeability.

(2) The ion electrode

The ion electrode is covered with the membrane, which is electrochemically deposited on the basic electrode and responds to hydrogen ions. Hydrogen ion responsable membranes are electropolymerized membranes such as 2,6-dimethylphenol, 4,4'-biphenol, 1,2-diaminobenzene, 1-aminopyrene, 1,8-diaminonaphthalene, 1,5-diaminonaphthalene etc..

In order to measure the concentration of hydrogen ions, this electrode is dipped together with a reference electrode such as a saturated calomel electrode into the solution, and the voltage between the two electrodes is measured.

(3) Bio-sensor

Figure 2A:
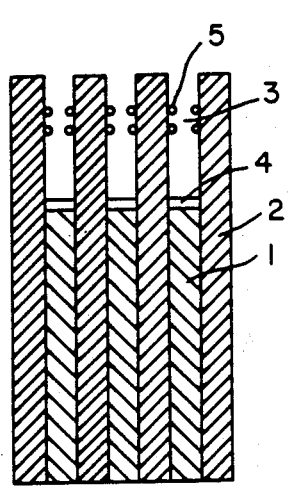
FIG. 2 shows a conceptual illustration of an electrode for a bio-sensor which is one of the definite applications of this invention.
Figure 2B:
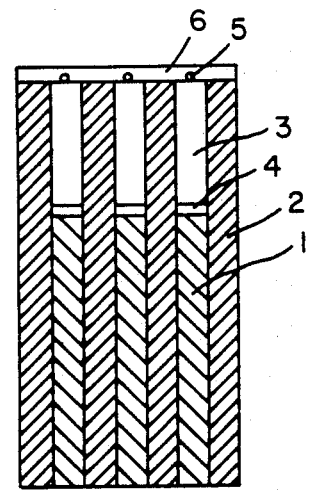

FIG. 2 shows an electrode for a bio-sensor. The said electrode is covered with a membrane 6, in which an enzyme or microorganism 5 is immobilized.

Or those are immobilized on the inside surfaces of microholes 3.

In the case of the potentiometry method, the enzyme is selected from urease, penicillinase, glucoseoxidase, lipase etc.. And in the case of the amperometry method, the enzyme is selected from glucoseoxidase, latic acid oxidase, L-aminooxidase, xanthionoxidase, uric acid oxidase, pyruvate oxidase, lactate oxidase etc. including each kind of oxidasic enzyme.

Immobilized membrane 6 is selected from polyvinyl chloride, polyacrylamide, acetylcellulose, cellulose triacetate, cross linked polyvinylalcohol etc. Not only the membrane but also the fiber mass of Nylon or its mesh may be applicable.

The enzyme or microorganism is immobilized with the membrane by means of adsorption or inclusion, or making a covalent linkage, or making a cross link by glutaraldehyde.

In the case the enzyme or microorganism is immobilized onto the inside surfaces of the micro-holes of the nonconducting materials, the enzyme is bonded to the functional group (amino group, for example) of the epoxy resin. In order to make a bio-sensor, the enzyme immobilized electrode and the counter electrode of silver/silver chloride are combined.

(4) Reference electrode

In the case of a reference electrode, silver and silver halide are deposited on the basic electrode surface. Chlorine and bromine are preferable as halogens. More preferably micro-holes are filled with gelatinoid material, as mentioned hereinbefore. And it is most preferable that a salt with a halogen ion can be included in the gelatinoid material. Examples of the present invention and comparative examples are illustrated below.

EXAMPLE 1, 2, 3 AND COMPARATIVE EXAMPLE 1

The bundle of one thousand carbon fibers ("Torayca T-300 1K", having diameters of 7 μm) was impregnated with epoxy resin including a hardening agent. This impregnated bundle of fibers was hardened after heating while being stretched, so that a composite material like a wire having a diameter of about 0.3 mm was obtained. After the side face of this wire was insulated by epoxy resin completely, it was cut and one cross sectional face was burnished by the conventional method, and another end was bonded to the lead wire by silver paste, then the electrode was made.

This burnished part was dipped in a sulfuric acid aqueous solution (2 mM) and by using the platinum wire as the counter electrode anodic oxidation was executed under the conditions described below. The dependence of the flow rate of the solution on the current of oxygen reduction was investigated using the obtained sensor. Namely, a beaker with a magnetic stirrer was filled with saline, and the above-mentioned sensor was used as the working electrode and the silver/silver chloride was used as the counter electrode, then the solution was contacted with air at room temperature to be saturated with air.

A negative voltage of 0.6 volt(vs Ag/AgCl) was applied at the working electrode, and the flowing cathodic current was measured. The current was measured respectively when the magnetic stirrer was revolved as fast as it could be and when it was stopped and the ratio was obtained.

In Example 1 operations to oxidize at 1.75 volt for 15 minutes, then to reduce at −1.2 volt for 1 minute, were repeated thirty-five times.

In Example 2 after oxidizing at 0.03 mA for 80 minutes it was reduced at −0.7 volt for 10 minutes in saline.

In Example 3 after oxidizing at 0.5 mA for 9 minutes it was reduced at −0.6 volt for 10 minutes.

The depth of the micro-hole in each electrode was 120 μm in Example 1, 150 μm in Example 2, 240 μm in Example 3.

The measured value using the electrode before the anodically etching treatment as Comparative Example was shown.

The result is shown in Table 1.

TABLE 1

| | Value of current when the solution flows divided by the current when the solution stops |
|---|---|
| Example 1 | 1.40 |
| Example 2 | 1.36 |
| Example 3 | 1.32 |
| Comparative Example 1 | 6.02 |

EXAMPLE 4

By using a bundle of one thousand carbon fibers ("Torayca T-300", having the diameter of 7 μm), the composite material like a wire with a diameter of about 0.3 mm was obtained by means of same procedure as described in Example 1.

This wire was cut and the one side was burnished by means of a conventional method, another end was bonded to the lead wire by silver paste. The burnished part was dipped in a sulfuric acid aqueous solution (2 mM) using platinum wire as the counter electrode and it was oxidized electrochemically at 0.5 mA for 9 minutes and then reduced at −0.6 volt for 20 minutes.

On observation of a scanning electron microscope (SEM), the depth of the etched part of carbon fibers was about 100 μm, and the surface of the electrode was sharp like a pencil.

The thin layer of platinum was made on the above-stated micro-hole electrode by the method which is explained hereinafter. Namely, the micro-hole electrode was dipped in an aqueous solution containing chloro-platinic acid (0.037 mol./l), ammonium phosphate (0.134 mol./l) and sodium phosphate (0.704 mol./l), and the current was run in the amount of 8 mC using platinum as the counter electrode. Then the electrode obtained was well washed with deionized water. On observation by SEM, a platinum thin layer of about 0.6 μm adhered on the electrode unifomly.

Figure 3:
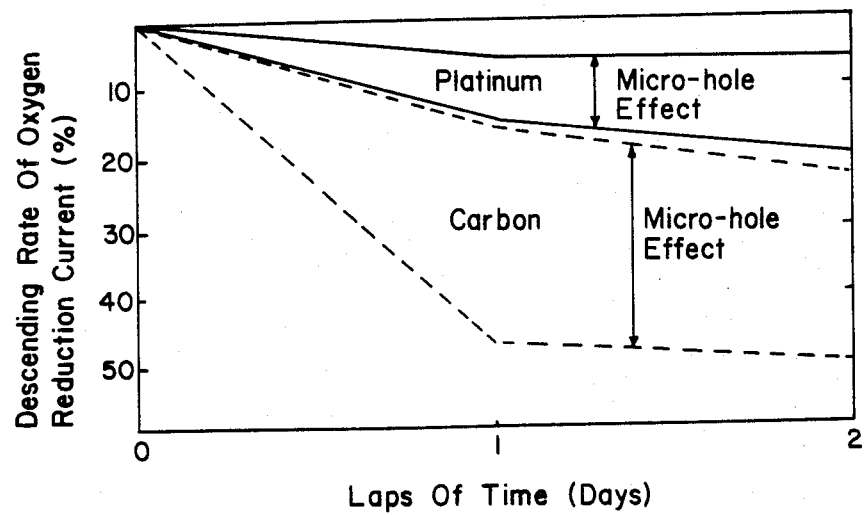
FIG. 3 shows contamination by interference substances of each electrode which has micro-holes, and which has not, this has been carried out in Example 4.

FIG. 3 shows that the progress of the electrode contamination when an electrode after plating with platinum (represented by "Platinum" in the FIG.) and electrode before plating with platinum (represented by "Carbon" in the FIG.) were left in the LB culture composition (37° C.).

The carbon electrode was shown by a dotted line and the platinum electrode was shown by a solid line. Each lower line showed the value where the electrode didn't have micro-holes and the upper line showed the value when the electrode had micro-holes, the depth of which was about 100 μm. In each case, the decreasing rate of oxygen reduction current was low when micro-holes were present (micro-hole effect). It is supposed that the micro-hole has the effect of a filter which makes electrode contaminants difficult to pass.

About the above-mentioned electrode which was plated with platinum, the decrease of oxygen reduction current was about 5% till 24 hours later, then oxygen reduction current was constant.

A thin membrane of polyaniline was electrochemically deposited on the above-mentioned electrode plated with platinum.

Namely the micro-hole electrode was dipped in an acetonitrile solution containing aniline (0.01 mol./l), sodium perchlorate (0.1 mol./l) and pyridine (0.02 mol./l), then polymerization was accomplished until the current couldn't run at 1.2 volt (vs. SCE). On observation by SEM, it was certified that a thin polymer membrane was formed on platinum.

When that electrode obtained was left in the LB culture composition at 37 C for 10 days, after the sterilizations (120° C., for 20 minutes), decrease of the value of oxygen reduction current wasn't observed at all. And there was no trouble even when the sterilization was repeated 10 times.

EXAMPLE 5

The same electrode as in Example 1 was made except that the diameter of the carbon fiber was 5 μm.

The burnished part was dipped in a sulfuric acid aqueous solution (2 mM) using a platinum wire as the counter electrode and it was oxidized electrochemically at a constant current of 0.2 mA. The carbon fibers were etched about 100 μm. Then it was allowed to stand at −0.7 volt for 20 minutes.

Similarly, an electrode of carbon fiber etched about 100 μm was made, using each bundle of one hundred fibers having diameters of 20 μm and 30 μm respectively.

Negative charge (−0.7 v) was applied at each electrode using an electrode of silver/silver chloride as the counter electrode in a solution of LB culture composition. A decreasing rate of oxygen reduction current was obtained after 24 hours. The result is shown in Table 2. This decreasing rate is small when the micro-hole is small.

TABLE 2

| the diameter of carbon fiber (μm) | the descending rate of oxygen reduction current (%) |
|---|---|
| 5 | 10 |
| 7 | 15 |
| 20 | 35 |
| 30 | 50 |

EXAMPLE 6

Each electrode was made by the same method as Example 4 except using phenol, 2,5-dimethyl phenol, 4,4'-diaminodiphenyl ether instead of aniline. Though it was left in LB culture composition at 37° C. for 10 days, decrease of the value of the oxygen reduction current wasn't observed.

EXAMPLE 7

A bundle of three thousand carbon fibers ("Torayca T-300", having a diameter of 7 μm) was put into a polyethylene tube (inside diameter 2 mm) of 35 cm length, and one end of carbon fibers was fixed outside of the tube. An epoxy resin (produced by Toray-Hysol Co. Ltd.,) containing hardening agent was poured from the inlet where the carbon fibers were fixed. This was post-cured on about 6020 C. for one hour and a half, then a hardened carbon fiber composite material was pulled out from the tube, and cut into 10 cm length. Next, it was treated with heat in an electric furnace. One end of this carbon fiber composite material was bonded to the lead wire by silver paste, and another end was burnished by means of conventional method after the side face was insulated completely by epoxy resin.

A part of the carbon fibers were removed by anodic oxidation of this electrode in a sulfuric acid aqueous solution (2 mM) using a platinum plate as the counter electrode. The anodic oxidation was done at constant current 1 mA for 10 minutes and twenty minutes respectively. The depth of micro-hole was 90 μm at 10 minutes, and was 140 μm at 20 minutes. Negative charge (−0.6 v) was applied at this electrode in a saline by using silver/silver chloride as the counter electrode, then the value of dissolved oxygen reduction current was measured. Thereafter a value of the current when the solution was stirred, divided by the current when it stopped was obtained. The values were 1.57 and 1.34 respectively when anodic oxidation was done for 10 and 20 minutes.

EXAMPLE 8

A composite material of carbon fiber and epoxy resin was made similarly as Example 1 except that the number of fibers was three thousand. When this carbon fiber composite material was oxidized anodically at constant current (1 mA) in a sulfuric acid aqueous solution (2 mM) using platinum plate as the counter electrode, the carbon fibers were etched about 200 μm. Next, plating with platinum was done on the carbon fibers like Example 4 by the amount of 12 mC.

The temperature dependance of the value of oxygen reduction current at this electrode was less than 0.8%/°C. This value was smaller than that the Clark oxygen sensor which was in the range of from 4 to 5%/°C. (Cf. "The optimum measuring and control of the fermentation process" Science Forum Page 214).

The end of this electrode was dipped in polyvinyl chloride (produced by Kanto Chemical Co. Ltd.,) 8 wt% solution (dimethylformamide), and was left in methanol for 3 hours. Then, after it was washed well by deionized water, it was left in 20 cc of phosphate buffer solution (0.066M) containing glucose oxidase 5 mg (produced by Nagase Co. Ltd.,) for 10 hours. It was washed by deionized water, and −0.6 v was applied (vs. SCE) in a phosphate buffer solution (0.066M) using a saturated calomel electrode as the reference electrode and platinum wire as the counter electrode. At this time, the relationship between the concentration of glucose and the decrease of oxygen reduction current was linear. It took sixty seconds for the current to become constant. The rate of change of the current with temperature change of the solution was 1.4%/°C.

When the potential (which was applied at this enzyme electrode) was changed to +0.6 V (vs. SCE), the relation of the glucose concentration and oxidation current (current of hydrogen peroxide oxidization) was a good linear relationship by our investigation.

EXAMPLE 9

A carbon fiber composite material was made by the same method as Example 8, and the carbon fibers were etched about 200 μm. And at once the material was dipped in 20 cc of phosphate buffer solution (0.066M) containing glucose oxidase 10 mg for 10 hours. It was washed well by deionized water, and the relation of the glucose concentration and the amount of the decrease of oxygen reduction current like Example 6 was a straight line passing the zero point. The changed rate of current by temperature change of solution was 1%/°C.

EXAMPLE 10

A carbon fiber composite material was formed using a bundle of one thousand carbon fibers ("Torayca T-300", having a diameter of 7 μm) like Example 1.

This composite material was oxidized electrochemically at a constant current (0.34 mA) in a sulfuric acid aqueous solution (2 mM), and anodically etched about 200 μm.

A polymer membrane was electrochemically deposited at 1.5 volt (vs. SCE) for 10 minutes in acetonitrile solution containing 2,6-dimethylphenol (20 mM) and sodium perchlorate (0.2M) using platinum wire as the counter electrode, and a saturated calomel electrode as the reference electrode. The potential in various pH solutions was investigated by using this electrode, and a good linear relationship with an inclination of −56 mV/pH was obtained. It responded in 1 minute when the electrode was removed from a pH2 solution to a pH10 solution.

COMPARATIVE EXAMPLE 2

The constancy of potential was investigated by using the same pH electrode as Example 10 and the same one (except without micro-holes) in the phosphate buffer solution which includes a yeast extract essence (0.5 wt %), bactotrypton (0.3 wt %). As the result, the electrode with micro-holes gave a stable potential, but that without micro-holes gave a potential slip, and its error was 50 mV.

EXAMPLE 11

The same electrode, except that the depth of etching was 100 μm, was formed. This electrode was plated with platinum by the amount of 4 mC as described in Example 4.

A polymer was electrochemically deposited on this electrode at 1.0 volt (vs. SCE) potential in the phosphate buffer solution (2 M, pH=7) which contains 1,2-diamino benzene (20 mM) for 10 minutes, using platinum wire as the counter electrode and saturated calomel electrode as the reference electrode. As by using this electrode the potential was investigated in solutions having various pH values, and a good linear relation having an inclination of −53 mV/pH was obtained during pH4 and pH9.

INDUSTRIAL APPLICABILITY

The minute electrode of this invention is useful for various electrode used in electrochemical analysis, and it is suitable especially for an electrode for measuring the concentration of dissolved oxygen, for the concentration of ions, for bio sensors, or for reference electrodes.

We claim:

1. A minute electrode for electrochemical analysis characterized in that it is comprised of a bundle of carbon fibers covered with a nonconducting resin, wherein ends of said carbon fibers are recessed from one end of the resin and wherein micro-holes extending to the outside in the direction of the longitudinal axis of the bundle of fibers are provided.

2. The minute electrode according to claim 1, wherein the diameter of the carbon fibers is less than 20 μm.

3. The minute electrode according to claim 1, wherein the depth of micro-holes is in the range of from 0.5 to 500 μm.

4. The minute electrode according to claim 1, wherein the nonconducting resin comprising a high molecule material is selected from the group consisting of fluorinated resins, polyester resins, epoxy resins, polyphenylene oxide resins, polyphenylene sulfide resins, urethane resins, silicon resins, vinyl chloride resins and phenol resins.

5. The minute electrode according to claim 1, wherein a surface of the end of a recessed carbon fiber is covered with a selective permeable membrane.

6. The minute electrode according to claim 5, wherein the selective permeable membrane is an electropolymerized membrane.

7. The minute electrode according to claim 6, wherein the electropolymerized membrane is adapted for measuring the concentration of dissolved oxygen.

8. The minute electrode according to claim 6, wherein, said electropolymerized membrane responds to the hydrogen ion for measuring concentration thereof.

9. The minute electrode according to claim 1, 2, 3, 4, 5, 6, 7 or 8, wherein an enzyme or microorganism is immobilized near the ends of the recessed carbon fibers or on the inside surfaces of said micro-holes.

10. The minute electrode according to claim 1 for reference electrode, wherein the surface of the recessed carbon fibers is covered with silver and silver halide.

11. A minute electrode for electrochemical analysis comprising:
a bundle of longitudinally extending carbon fibers and a non-conducting resin surrounding each of said fibers, wherein the fibers at one end of said electrode are recessed from the resin, thereby forming a multiplicity of micro-holes extending in the direction of the longitudinal axis of the bundle of fibers in the end of said electrode.

12. A minute electrode for electrochemical analysis comprising a multiplicity of longitudinally extending carbon fibers embedded in a non-conducting resin, thereby forming an islands-in-a-sea configuration, the fibers in one end of said electrode being recessed from the end of said resin and thereby forming a multiplicity of micro-holes extending in the direction of the longitudinal axis of the multiplicity of fibers.

* * * * *